(12) United States Patent
Makino et al.

(10) Patent No.: US 11,662,313 B2
(45) Date of Patent: *May 30, 2023

(54) MICROFLUIDIC DEVICES AND OBSERVATION METHODS

(71) Applicant: TOPPAN PRINTING CO., LTD., Taito-ku (JP)

(72) Inventors: Yoichi Makino, Taito-ku (JP); Keisuke Goto, Taito-ku (JP)

(73) Assignee: TOPPAN PRINTING CO., LTD., Taito-ku (JP)

( * ) Notice: Subject to any disclaimer, the term of this patent is extended or adjusted under 35 U.S.C. 154(b) by 0 days.

This patent is subject to a terminal disclaimer.

(21) Appl. No.: 16/018,277

(22) Filed: Jun. 26, 2018

(65) Prior Publication Data

US 2018/0299380 A1  Oct. 18, 2018

Related U.S. Application Data

(63) Continuation of application No. PCT/JP2016/089173, filed on Dec. 28, 2016.

(30) Foreign Application Priority Data

Dec. 28, 2015  (JP) .............................. JP2015-257264

(51) Int. Cl.
*G01N 21/64*  (2006.01)
*C12Q 1/68*  (2018.01)
(Continued)

(52) U.S. Cl.
CPC ...... *G01N 21/645* (2013.01); *B01L 3/502715* (2013.01); *C12Q 1/25* (2013.01);
(Continued)

(58) Field of Classification Search
CPC ....... B01L 2300/0829; B01L 3/502715; B01L 2300/0877; B01L 2300/168;
(Continued)

(56) References Cited

U.S. PATENT DOCUMENTS 11,097,269 B2 * 8/2021 Goto .................. G01N 21/6428
2005/0100270 A1 * 5/2005 O'Connor ................ G02B 3/14
385/19

(Continued)

FOREIGN PATENT DOCUMENTS

JP    2004-309405 A    11/2004
JP    2008-14688 A     1/2008
(Continued)

OTHER PUBLICATIONS

International Search Report dated Mar. 14, 2017 in PCT/JP2016/089173, filed Dec. 28, 2016, 5 pages.

(Continued)

*Primary Examiner* — Jennifer Wecker
*Assistant Examiner* — Bryan Kilpatrick
(74) *Attorney, Agent, or Firm* — Oblon, McClelland, Maier & Neustadt, L.L.P.

(57) ABSTRACT

A microfluidic device includes a substrate having an electromagnetic wave transmission property, a lid member facing the substrate and being separated from the substrate such that a flow channel is formed between the substrate and the lid member, a light absorption layer which is placed in the flow channel and absorbs an electromagnetic wave, and a microwell array formed on the substrate and having plural microwells that are open to the flow channel to receive a target of analysis.

20 Claims, 8 Drawing Sheets

(51) Int. Cl.
*G01N 33/487* (2006.01)
*B01L 3/00* (2006.01)
*G01N 21/05* (2006.01)
*G01N 35/08* (2006.01)
*C12Q 1/25* (2006.01)

(52) U.S. Cl.
CPC ............... *C12Q 1/68* (2013.01); *G01N 21/05* (2013.01); *G01N 21/6428* (2013.01); *G01N 33/487* (2013.01); *G01N 35/08* (2013.01); *B01L 2300/0829* (2013.01); *B01L 2300/0877* (2013.01); *B01L 2300/0887* (2013.01); *B01L 2300/165* (2013.01); *G01N 2021/058* (2013.01); *G01N 2021/6482* (2013.01)

(58) Field of Classification Search
CPC ......... G01N 21/6428; G01N 2021/058; G01N 2021/6439; G01N 21/6452; G01N 33/52; B81B 1/006; B81B 2203/0338; B81B 2203/0353; B81B 3/0083; B81B 1/00; B81C 1/00
See application file for complete search history.

(56) References Cited

U.S. PATENT DOCUMENTS

| | | |
|---|---|---|
| 2009/0263807 A1 | 10/2009 | Yotoriyama |
| 2012/0015828 A1* | 1/2012 | Ozawa ................ B01L 3/50273 |
| | | 506/7 |
| 2012/0039774 A1 | 2/2012 | Yotoriyama et al. |
| 2012/0208292 A1 | 8/2012 | Lewis et al. |
| 2016/0333400 A1 | 11/2016 | Makino et al. |
| 2018/0221877 A1* | 8/2018 | Goto ..................... G01N 21/03 |

FOREIGN PATENT DOCUMENTS

| | | |
|---|---|---|
| JP | 2009-210265 A | 9/2009 |
| JP | 2010-271304 A | 12/2010 |
| JP | 2013-528805 A | 7/2013 |
| WO | WO 2015/047190 A1 | 4/2015 |
| WO | WO 2015/115635 A1 | 8/2015 |

OTHER PUBLICATIONS

Office Action dated Jul. 14, 2020 in corresponding Japanese Patent Application No. 2017-559246 (with English Translation), 10 pages.

* cited by examiner

MICROFLUIDIC DEVICES AND OBSERVATION METHODS

CROSS-REFERENCE TO RELATED APPLICATIONS

The present application is a continuation of International Application No. PCT/JP2016/089173, filed Dec. 28, 2016, which is based upon and claims the benefits of priority to Japanese Application No. 2015-257264, filed Dec. 28, 2015. The entire contents of these applications are incorporated herein by reference.

BACKGROUND OF THE INVENTION

Field of the Invention

The present invention relates to microfluidic devices and observation methods, and in particular, relates to a technique suitable for use with biomolecule analysis kits.

Discussion of the Background

In recent years, measurement of biomaterials and cells by using fluorophores are performed for research and diagnosis purposes. For example, the fluorescence in situ hybridization (FISH) method, which is a technique by which fluorescence-labelled oligonucleotide probes are hybridized to target genes before the target genes can be detected by fluorescence microscopy, is used for cancer diagnosis.

For example, PTL 1 describes that digital ELISA is a technique by which single protein molecules are introduced into microwells, which are then observed by fluorescence microscopy to count the wells that accommodate protein molecules, and the technique enables protein detection by enzymatic reaction performed in microchambers having a volume of 1 picoliter (pl) or less. Further, PTL 2 describes a method for detecting a difference in a single base in genes by performing an Invader reaction in microchambers.

PTL 1: JP-2004-309405 A
PTL 2: WO 2015/115635

SUMMARY OF THE INVENTION

According to an aspect of the present invention, a microfluidic device includes a substrate having an electromagnetic wave transmission property, a lid member facing the substrate and being separated from the substrate such that a flow channel is formed between the substrate and the lid member, a light absorption layer which is placed in the flow channel and absorbs an electromagnetic wave, and a microwell array formed on the substrate and having plural microwells that are open to the flow channel to receive a target of analysis.

BRIEF DESCRIPTION OF THE DRAWINGS

A more complete appreciation of the invention and many of the attendant advantages thereof will be readily obtained as the same becomes better understood by reference to the following detailed description when considered in connection with the accompanying drawings, wherein.

DESCRIPTION OF THE EMBODIMENTS

Figure 1:
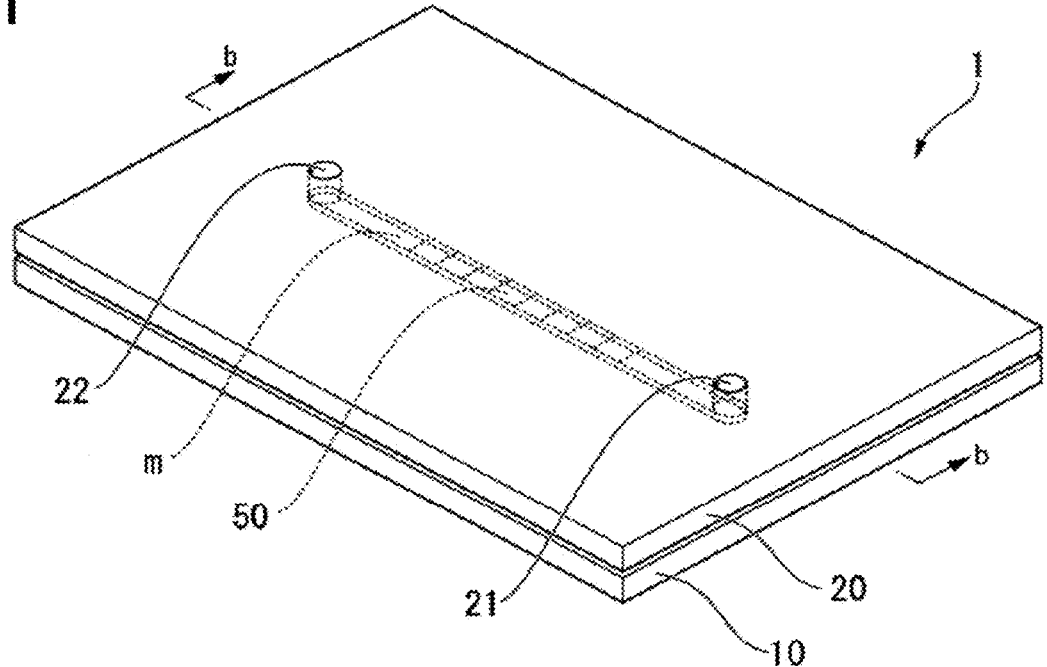
FIG. 1 is a perspective view of a microfluidic device according to a first embodiment of the present invention.

The embodiments will now be described with reference to the accompanying drawings, wherein like reference numerals designate corresponding or identical elements throughout the various drawings.

With reference to the drawings, a microfluidic device and an observation method according to a first embodiment of the present invention will be described. In the following description, the dimensions in the drawings may be exaggerated for the purpose of illustration, and may not necessarily be to scale.

Figure 2:
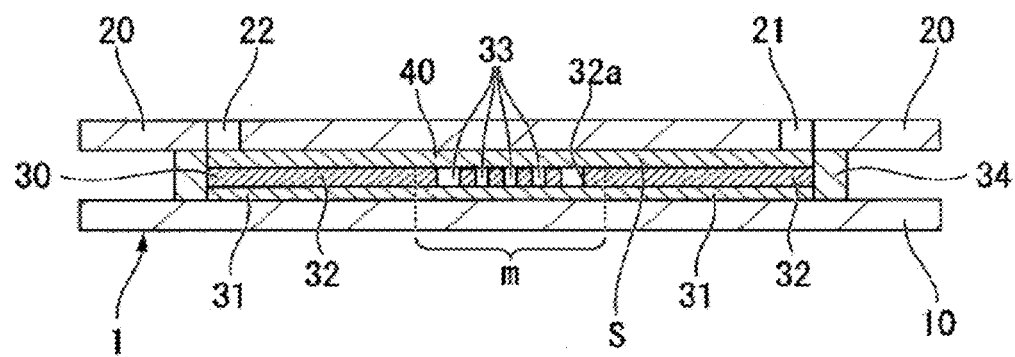
FIG. 2 is a cross-sectional view of the microfluidic device according to the first embodiment of the present invention.

FIG. 1 is a perspective view of a microfluidic device according to the present embodiment, and FIG. 2 is a cross-sectional view of the microfluidic device according to the present embodiment (cross-sectional view taken along the line b-b of FIG. 1). In FIGS. 1 and 2, reference character 1 designates a microfluidic device.

The microfluidic device 1 according to the present embodiment is a biomolecule analysis kit to which a biomolecule analysis method can be applied. As biomolecules to be analyzed in the biomolecule analysis kit according to the present embodiment, any of cells, exosomes, DNAs, RNAs, miRNAs, mRNAs (hereinafter, also collectively referred to as RNAs), and proteins may be selected. The biomolecule analysis kit according to the present embodiment is, for example, an array device for nucleic acid quantification.

As shown in FIGS. 1 and 2, the microfluidic device 1 according to the present embodiment includes a substrate 10, a lid member 20 disposed to face the substrate 10, a microwell array (micropore array layer) 30 interposed between the substrate 10 and the lid member (cover) 20, and a light absorption layer 40 (a flow channel in which the light absorption layer 40 is disposed).

In other words, the microfluidic device 1 according to the present embodiment includes the substrate 10 having a first surface and a second surface located opposite to the first surface, the lid member 20 disposed to face the first surface of the substrate 10, the microwell array 30 interposed between the first surface of the substrate 10 and the lid member 20 and disposed on the first surface of the substrate 10, and the light absorption layer 40 (a flow channel in which the light absorption layer 40 is disposed).

The substrate 10 and the microwell array 30 constitute a reaction vessel.

Further, an area in which a plurality of microwells 33 are disposed is referred to as a microwell array area m.

The substrate 10 is a plate member made of a substantially transparent material and has electromagnetic wave transmission properties. The electromagnetic wave described herein includes X-rays, ultraviolet rays, visible rays, and infrared rays. By virtue of the electromagnetic wave transmission properties of the substrate 10, fluorescence, phosphorescence, and the like generated in a sample sealed in the microfluidic device 1 can be observed through the substrate 10 (the outer surface of the substrate 10, or the second surface of the substrate 10).

The electromagnetic wave transmission properties of the substrate 10 may be within a predetermined wavelength range. For example, for detection of fluorescence having a peak in a wavelength range of 350 to 700 nm, which is a visible light region, in a sample in the microwell, the substrate having transmission properties at least to visible light in the above wavelength range (350 to 700 nm) can be used.

Materials for forming the substrate 10 include, for example, glass, resin, and the like. Examples of the resin substrate include ABS resin, polycarbonate resin, COC (cycloolefin copolymer), COP (cycloolefin polymer), acrylic resin, polyvinyl chloride, polystyrene resin, polyethylene resin, polypropylene resin, polyvinyl acetate, PET (polyethylene terephthalate), PEN (polyethylene naphthalate), and the like. These resins may contain various additives, or alternatively, a plurality of resins may be mixed or laminated.

A thickness of the substrate 10 may be appropriately determined, and is for example preferably 5 millimeter (mm) or less, more preferably 2 mm or less, and still more preferably 1.6 mm or less.

The substrate 10 has at least sufficient rigidity to resist breakage during handling of an array device for nucleic acid quantification by a transport apparatus or manual handling by an operator.

Since the sample analysis method described later uses fluorescence or phosphorescence, it is preferred that the substrate 10 does not have autofluorescence at the wavelength used for detection of observation results or that the substrate 10 has weak autofluorescence which is insignificant for the detection of experiment results. For example, autofluorescence which is not more than one-half or not more than one-tenth of the fluorescence of the analysis target can be regarded as being insignificant for the detection of experiment results.

The lid member 20 may be in a plate, sheet, or film shape, and has a first hole (inlet port) 21 and a second hole 22 that penetrate the lid member 20 in the thickness direction. In the assembled microfluidic device 1, the first hole 21 and the second hole 22 communicate with an inner space (flow channel) S which includes the microwell array 30, and serve as an inlet port through which a fluid is supplied into the inner space and an outlet port through which a fluid is discharged, respectively.

Materials for forming the lid member 20 and a thickness of the lid member 20 may be the same as those of the substrate 10.

The lid member 20 is superposed on the substrate 10 so as to cover a plurality of openings of the reaction vessels while forming a gap between the lid member 20 and the substrate 10. A space between the substrate 10 and the lid member 20 serves as a flow channel through which various kinds of liquid pass. In the present embodiment, various kinds of liquid flow from the first hole 21 which is an inlet port to the second hole 22 which is an outlet port through the space between the substrate 10 and the lid member 20.

The electromagnetic wave transmission properties of the lid member 20 can be determined as appropriate. That is, when a step of emitting electromagnetic waves, which is described later, is not performed through the lid member 20 (outer surface of the lid member 20), the lid member 20 may not necessarily have electromagnetic wave transmission properties.

The microwell array 30 includes a bottom layer 31 disposed on the substrate 10, and a wall layer 32 formed on the bottom layer 31. The microwell array 30 has a plurality of microwells 33 arranged in array. In the inner space S between the substrate 10 and the lid member 20, a gap exists between the microwell array 30 and the lid member 20. This gap serves as a flow channel that communicates the plurality of microwells 33 with the first hole 21 and the second hole 22. In the microfluidic device 1 according to the present embodiment, the bottom layer 31 may not be provided.

The microwell array 30 is a layer in which a plurality of through holes are arranged. In the microwell array 30 according to the present embodiment, for example, a layer thickness of the microwell array 30 is 3 μm. Further, an interval of 100 μm between the bottom layer 31 and the lid member 20 is provided as a flow channel. The microwells 33, which serve as reaction vessels formed by the microwell array 30 and the substrate 10, are spaces of bottomed cylindrical shape with one end open.

According to the present embodiment, each microwell 33 has, for example, a cylindrical shape with 5 μm diameter and 3 μm height in the center axis direction (the volume of this microspace is approximately 60 femtoliter (fl)).

The volume of the microwell 33 as a reaction vessel may be appropriately set; however, the smaller the volume of the microwell 33, the more the reaction time until signal detection is possible can be shortened.

For example, the volume of the respective microwells 33 is 100 picoliter, or not more than 100 picoliter.

Furthermore, in the present embodiment, the configuration of the present embodiment is applicable for protein analysis.

A distance (pitch) between the centers of the respective microwells 33, which are the reaction vessels, may be larger than a diameter of the respective microwells 33.

An interval (gap) between the respective microwells 33 is determined depending on the resolution by which signal detection can be independently performed in the respective microwells 33.

The respective microwells 33 are arrayed in a triangular lattice in plan view (as viewed in the vertical direction) with respect to a main surface of the microwell array 30. The arrangement of the respective microwells 33 is not specifically limited.

When the bottom layer 31 is not provided, fine microwells 33 having a bottomed cylindrical shape are formed by the microwells 33 in the microwell array 30 and a surface of the substrate 10 such that the bottom of the cylindrical shape is formed by the substrate 10.

When the bottom layer 31 is provided, fine microwells 33 having a bottomed cylindrical shape are formed by the microwells 33 in the microwell array 30 and a surface of the bottom layer 31 such that the bottom of the cylindrical shape is formed by the bottom layer 31.

Specifically, for a shorter time required to saturate a signal and to generate a sufficient signal, the volume of the microwells 33 is set based on the amount of liquid at which the number of molecules to be analyzed becomes one or less per well.

Materials for the microwell array 30 may be resin, glass, and the like. Materials for the microwell array 30 may be the same as those of the substrate 10 or may be different from those of the substrate 10. Further, the microwell array 30 may be made of the same material as that of the substrate 10, and the microwell array 30 may be integrated with the substrate 10.

Further, the microwell array 30 may be made of the same material as that of the substrate 10, and the microwell array 30 may be integrally molded with the substrate 10. Examples of the material of the microwell array 30 made of resin include cycloolefin polymer, silicone, polypropylene, polycarbonate, polystyrene, polyethylene, polyvinyl acetate, fluororesin, and amorphous fluororesin. Note that these materials listed as examples for the microwell array 30 are merely illustrative, and do not limit the material of the microwell array 30.

Further, the microwell array 30 may be colored. With colored microwell array 30, light measurement such as fluorescence, luminescence, and light absorbance in the microwells 33 can be performed while reducing effect of light from the microwells 33 adjacent to the microwells 33 to be measured.

The microwells 33 as reaction vessels are formed in the microwell array 30 by applying a process such as etching, embossing, or cutting to a solid pattern of hydrophobic layer deposited on the substrate 10 (hydrophobic layer formed on the entire surface of the substrate 10). Further, when the microwell array 30 is molded integrally with the substrate 10, a portion of the microwell array 30 which corresponds to the microwells 33 is formed by applying a process such as etching, embossing, or cutting to the substrate 10. Thus, a pattern having a hydrophobic part or a hydrophilic part can be formed on the substrate.

When the bottom layer 31 is provided as the microwell array 30, the bottom layer 31 constitutes the bottom of the microwells 33. A hydrophilic material can be used for the bottom layer 31 to impart hydrophilicity to the bottom of the microwells 33, and a hydrophobic material can be used for the bottom layer 31 to impart hydrophobicity to the bottom of the microwells 33. If the properties of the bottom may be the same as those of the substrate 10, the wall layer 32 may be formed directly on the substrate 10 without providing the bottom layer 31. The bottom layer 31, if provided, is configured to have electromagnetic wave transmission properties so as not to disturb the observation of the sample in the microwells 33 through the substrate 10 (the outer surface of the substrate 10, or the second surface of the substrate 10).

In this case, the wall layer 32 can be formed by a colored material, or the wall layer 32 may have the same electromagnetic wave transmission properties as those of the substrate 10. The wall layer 32 has a plurality of arrayed through holes 32a as viewed in the thickness direction. The inner surfaces of the respective through holes 32a constitute the inner wall surfaces of the respective microwells 33.

As the material for forming the wall layer 32, a resin mixed with a colored component that absorbs electromagnetic waves of a predetermined wavelength can be used. Taking into consideration the properties required for the microwells 33, as with the bottom layer 31, either a hydrophilic resin in which the constituent molecules contain a hydrophilic group or a hydrophobic resin in which the constituent molecules contain a hydrophobic group can be used as the resin material.

Examples of the hydrophilic group include hydroxyl group, carboxyl group, sulfone group, sulfonyl group, amino group, amide group, ether group, ester group, and the like. For example, the hydrophilic resin may be selected as appropriate from siloxane polymer; epoxy resin; polyethylene resin; polyester resin; polyurethane resin; polyacrylic amide resin; polyvinyl pyrrolidone resin; acrylic resin such as polyacrylic acid copolymer; polyvinyl alcohol resins such as cationized polyvinyl alcohol, silanolated polyvinyl alcohol, and sulfonated polyvinyl alcohol; polyvinyl acetal resin; polyvinyl butyral resin; polyethylene polyamide resin; polyamide polyamine resin; cellulose derivatives such as hydroxy methyl cellulose and methyl cellulose; polyalkylene oxide derivatives such as polyethylene oxide and polyethylene oxide-polypropylene oxide copolymer; maleic anhydride copolymer; ethylene-vinyl acetate copolymer; styrene-butadiene copolymer; and combinations thereof and the like.

For example, the hydrophobic resin may be selected as appropriate from novolac resin; acrylic resin; methacrylic resin; styrene resin; vinyl chloride resin; vinylidene chloride resin; polyolefin resin; polyamide resin; polyimide resin; polyacetal resin; polycarbonate resin; polyphenylene sulfide resin; polysulfone resin; fluorine resin; silicone resin; urea resin; melamine resin; guanamine resin; phenolic resin; cellulose resin; and combinations thereof and the like.

Both the hydrophilic resin and the hydrophobic resin may be either a thermoplastic resin or a thermocurable resin. Moreover, resins curable with ionizing radiation such as electronic beam and UV light and elastomers may also be used. When a photoresist is used as the resin material, a plurality of fine through holes can be formed on the wall layer 32 with high precision by photolithography.

When a photoresist is not used, the wall layer 32 can be formed, for example, by injection molding or the like.

As the colored component, organic or inorganic pigments may be listed as examples. Specifically, black pigments include carbon black, acetylene black, and iron black; yellow pigments include chrome yellow, zinc yellow, yellow ocher, hansa yellow, permanent yellow, and benzine yellow; orange pigments include orange lake, molybdenum orange, and benzine orange; red pigments include red iron oxide, cadmium red, antimony vermilion, permanent red, lithol red, lake red, brilliant scarlet, and thioindigo red; blue pigments include ultramarine, cobalt blue, phthalocyanine blue, ferrocyanide blue, and indigo; green pigments include chrome green, viridian naphthol green, and phthalocyanine green.

A circumferential member 34 in a frame shape is disposed around the microwell array 30 in plan view (as viewed in the vertical direction). The dimension of the circumferential member 34 in the thickness direction of the microfluidic device 1 is larger than that of the wall layer 32. The circumferential member 34, which supports the lid member 20, forms a gap between the lid member 20 and the microwell array 30 to provide the flow channel.

Examples of material for the circumferential member 34 include, but are not limited to, silicone rubber, a double-sided adhesive tape formed by a core film made of an acrylic foam and acrylic adhesives applied on both surfaces of the core film, and the like.

Next, with reference to FIG. 3, a reagent composition which is favorably applicable to the microfluidic device 1, which is a biomolecule analysis kit according to the present embodiment, will be described.

A detection reaction reagent (liquid) 16*a* is an aqueous solution of a reagent that can be introduced into between the substrate 10 and a cover 20 through the inlet port 21. The detection reaction reagent 16*a* is a reagent for a biochemical reaction such as an enzymatic reaction with a template nucleic acid associated with the analysis target substance.

The biochemical reaction to a template nucleic acid is, for example, a reaction which causes signal amplification in the presence of template nucleic acid. The detection reaction reagent 16*a* is selected according to a method that can detect a nucleic acid, for example. For example, reagents used for the Invader (registered trademark) method, LAMP method (trademark), TaqMan (registered trademark) method, a fluorescence probe method and other methods are included in the detection reaction reagent 16*a* of the present embodiment.

Next, the light absorption layer 40 which is favorably applicable to the microfluidic device 1, which is a biomolecule analysis kit according to the present embodiment, will be described.

The light absorption layer 40 according to the present embodiment is a layer which is located on the openings of the microwells 33 to shield and absorb light corresponding to the observation light from the lid member 20 (outer surface of the lid member 20), which may be a disturbing factor observation of fluorescence in the microwells 33. The light absorption layer 40 may be solid, powder, fluid, or liquid, or may be disposed in the flow channel S as long as it is located on the openings of the microwells 33 and is capable of shielding light.

The light absorption layer 40 may be in contact with the microwell array 30 at a position near the microwells 33, and is preferably in contact with the entire circumference of the openings of the microwells 33. In other words, the light absorption layer 40 may be positioned so as to cover the openings of the microwells 33.

Although the light absorption layer 40 is preferably filled until it reaches the lid member 20 in the flow channel S, the light absorption layer 40 may not be necessarily in contact with the entire surface of the lid member 20 in the flow channel S.

Further, the thickness of the light absorption layer 40 is defined by the height dimension of the flow channel S. The necessary light shielding and absorbing ability can be determined depending on the light absorbance of the properties of the light absorption layer 40, which is described later.

Specifically, in the present embodiment, the light absorption layer 40 in the microfluidic device 1, which is a biomolecule analysis kit, may be liquid containing a light absorbent substance (light absorbent material). As a result, only the fluorescence emitted from the observation surface can be observed, while light emitted from the detection reaction reagent 16*b* outside the observation surface, which is the microwells 33, is not observed.

In addition to that, as the light absorption layer 40, liquid such as an oil-based sealant that is not miscible with the sample which contains the analysis target substance is selected from among the solutions that can be introduced into between the substrate 10 and the cover 20 through the inlet port 21. The oil-based sealant provided as the light absorption layer 40 can seal the microwells 33 in which the detection reaction reagent (aqueous solution) 16*a* is introduced.

The oil-based sealant as the light absorption layer 40 can be selected from materials that are not miscible with the sample containing the analysis target substance. The oil-based sealant may be mineral oil, chloroform, squalene, hexadecane, or fluorinated liquid such as FC40.

The light absorbent substance contained in the light absorption layer 40 is a substance that absorbs excitation light or wavelength to be observed and can be selected from materials soluble in the oil-based sealant. The light absorbent substance can be selected from pigment, dye, quencher (excitation energy absorbing agent), and the like.

The light absorbent substance contained in the light absorption layer 40 is preferably a black substance in view of light absorbency. However, any substance of blue, red, yellow, violet, green, or a combination color thereof can be selected depending on the light (electromagnetic waves) to be absorbed may also be selected.

In the light absorption layer 40, the light absorbance of the light absorption layer 40 can be selected depending on the magnitude of the autofluorescence or excitation light, which may disturb observation, and may be in the range of 0.05 or more, and more preferably 0.1 or more.

Here, the light absorbance may be measured by a measurement method using a spectrophotometer.

In the light absorption layer 40, a turbidity of the light absorption layer 40 can be selected depending on the magnitude of the autofluorescence or excitation light, which may disturb observation, and may be in the range of 50 to 5000, and more preferably approximately 200 to 2000.

Here, the turbidity may be measured by transmittance turbidimetry, transmittance light measurement, or scattered (reflected) light measurement method.

By use of the light absorption layer 40, an S/N ratio in the microfluidic device 1 during fluorescence observation can be in the range of 1.5 to 2000, and more preferably approximately 2 to 500.

In order to achieve the above light absorbance in the light absorption layer 40, when a particulate substance is selected as the light absorbent substance contained, the substance may have a particle diameter in the range of 5 μm or less, and more preferably approximately 0.01 μm or less so as not to disturb fluorescence observation in the microwells 33.

When a particulate substance is selected as the light absorbent substance contained in the light absorption layer 40, a concentration of the particulate substance to the oil-based sealant can be in the range of 0.01 to 30 vol %, and more preferably approximately 0.01 to 10 vol %. This concentration is a percentage of the weight of the particulate substance to the volume of the oil-based sealant.

Further, when a particulate substance is selected as the light absorbent substance contained in the light absorption layer 40, the concentration of the particulate substance to the oil-based sealant can be calculated as wt % concentration, which may be in the range of 0.001 to 50 wt %, and more preferably in the range of approximately 0.01 to 15 wt %. This concentration is a percentage of the weight of the particulate substance to the weight of the oil-based sealant.

When a pigment is used as the colored component contained in the light absorption layer 40 with the concentration in the above range (0.01 to 50 wt %), the grain size of the pigment may be determined in a predetermined range depending on the size of the microwell 33. For example, the grain size is preferably not more than one-fifth of the dimension in the radial direction of the opening of the microwell 33 (length in the radial direction) so as not to affect the observation precision in the microwells 33. The grain size is more preferably not more than one-tenth of the dimension in the radial direction of the opening of the microwell 33 (length in the radial direction). For example, if the radial direction of the microwell 33 is in the range of approximately 0.1 μm to 10 μm, the grain size of the pigment is preferably in the range of approximately 1 nm to 1 μm based on the value specified in the manufacturer catalogue or the like. If the radial direction of the microwell 33 is in the range of approximately 100 nm to 10 μm, the grain size of the pigment is preferably in the range of approximately 10 nm to 0.1 μm based on the value specified in the manufacturer catalogue or the like.

With the grain size in the above range (not more than one-fifth of the dimension in the radial direction of the opening of the microwell 33 (length in the radial direction), the pigment is sufficiently small relative to the microwell 33. As a result, pigment particle does not disturb observation of the microwells 33, ensuring observation with high precision. Further, by decreasing the area of the uncolored oil-based sealant provided between the pigment particles to be sufficiently small relative to the microwells 33, unnecessary fluorescence can be appropriately suppressed.

With reference to the drawings, an observation method of the present embodiment will be described below.

Figure 3:
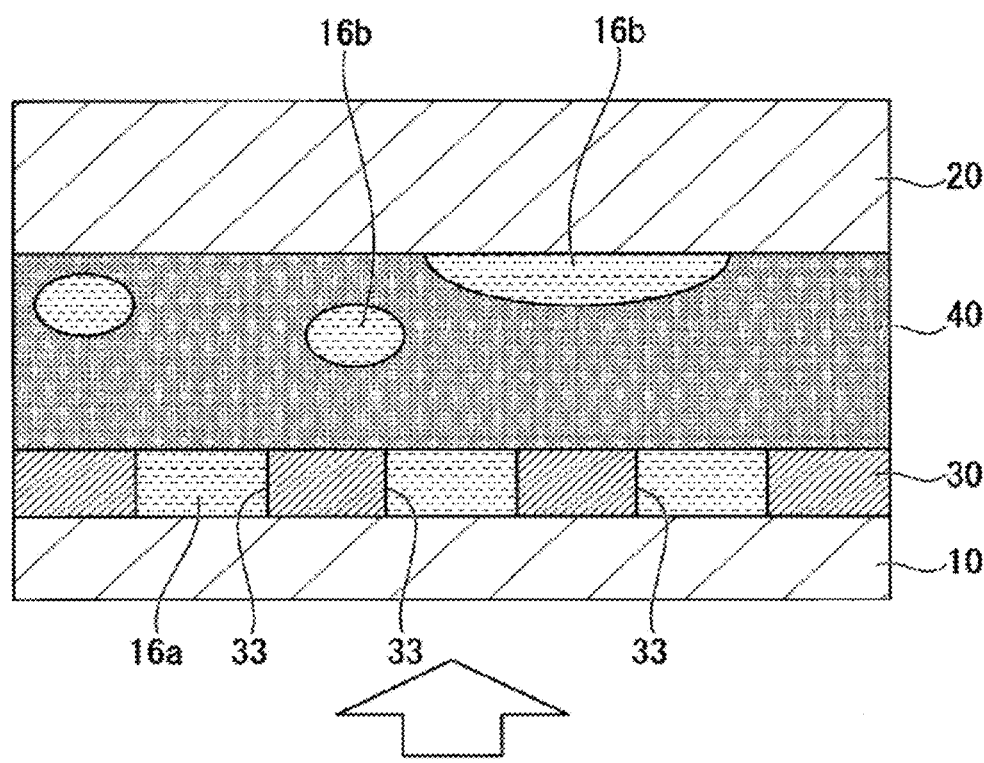
FIG. 3 is an enlarged cross-sectional view of the microfluidic device and an observation method according to the first embodiment of the present invention.

FIG. 3 is an enlarged cross-sectional view of an observation method by the microfluidic device 1 according to the present embodiment.

An observation method of the present embodiment includes supplying aqueous liquid into the flow channel of the microfluidic device 1 to introduce the aqueous liquid into the microwells 33 of the microwell array 30, forming the light absorption layer 40 as a sealant in the flow channel to form the light absorption layer 40 as a sealing layer on the upper side of the aqueous liquid introduced into the microwells 33 to thereby seal the aqueous liquid in the microwells 33, irradiating electromagnetic waves (first electromagnetic waves) onto the microwells 33, and detecting second electromagnetic waves (for example, fluorescence or phosphorescence) emitted from the microwells 33 by observation through the substrate 10.

In other words, the observation method of the present embodiment includes preparing the microfluidic device 1, supplying aqueous liquid into the flow channel of the microfluidic device 1 to introduce the aqueous liquid into the microwells 33, forming the light absorption layer 40 as a sealant in the flow channel to form the light absorption layer 40 as a sealing layer on the aqueous liquid introduced into the microwells 33 to thereby seal the aqueous liquid in the microwells 33, irradiating electromagnetic waves (first electromagnetic waves) onto the microwells 33, and detecting second electromagnetic waves (for example, fluorescence or phosphorescence) emitted from the microwells 33.

The aqueous liquid described above includes water, a biological sample such as a buffer solution containing biomolecules to be detected, enzymatic reaction liquid, the aforementioned detection reaction reagent 16a, and the like. Moreover, the aqueous liquid may contain additives such as surfactant.

Further, the sealant refers to liquid used to isolate the liquid introduced into the respective wells of the microwell array from each other so that the liquid introduced into the respective wells of the microwell array are not mixed with each other. The sealant may be oils, for example.

The sealant preferably has a contact angle to the material of the wall layer 32 in the range of 5 to 80 degrees. When the contact angle of the sealant is in the above range (5 to 80 degrees), a sample can be favorably sealed in the respective microwells 33. The contact angle of the sealant may be measured by using a sealant instead of water, for example, in accordance with the sessile drop method stipulated in JIS R3257-1999.

Examples of the oil used as a sealant include oil manufactured by Sigma Corporation under the trade name of FC40, oil manufactured by 3M Co., Ltd. under the trade name of HFE-7500, mineral oil used for PCR reaction, and the like. In the conventional microwell array, there may be difficulty in using mineral oil as a sealant. However, according to the above microwell array, mineral oil can be used as a sealant to seal aqueous liquid in the well.

As described above, in the present embodiment, a solution in which a colored component such as pigment is contained in the oil-based sealant can be applied to the light absorption layer 40.

First, aqueous liquid is supplied through the inlet port 21 of the microfluidic device 1 by using a syringe or the like. As a result, the aqueous liquid 16 is introduced into the respective microwells 33 of the microwell array 30 disposed in the flow channel.

Figure 13:
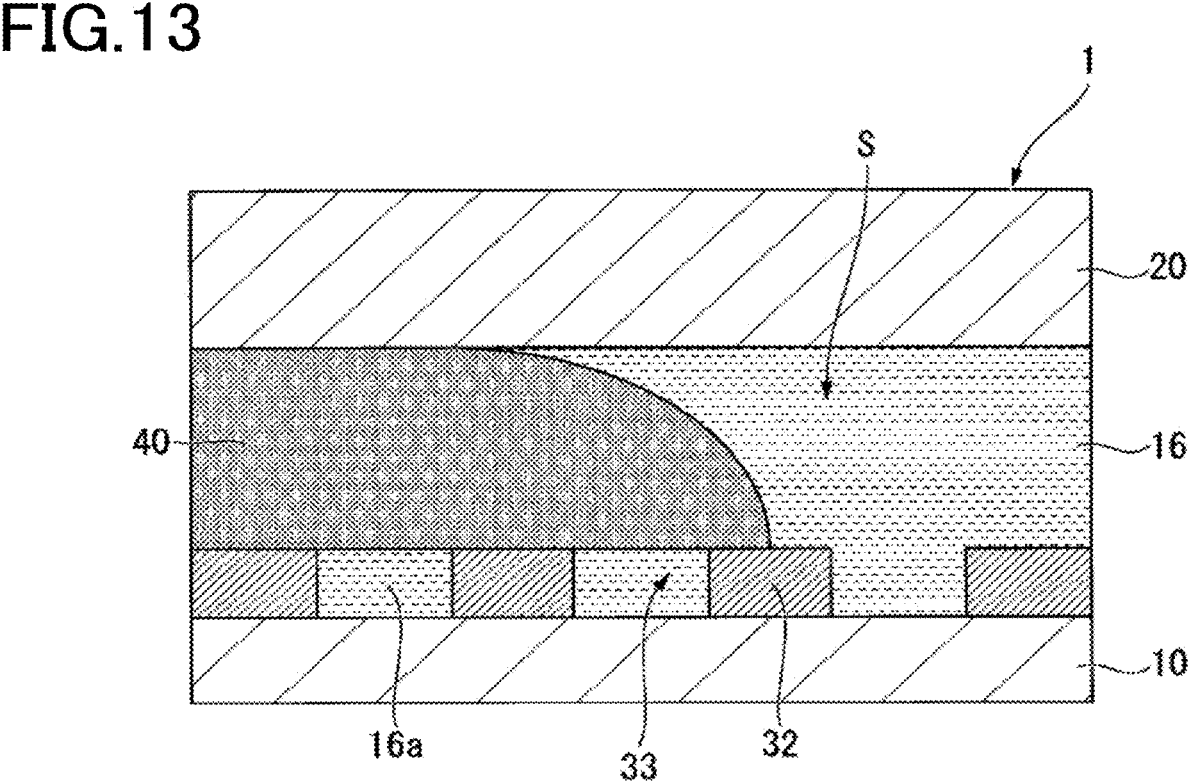
FIG. 13 is a view which illustrates the microfluidic device in use according to the first embodiment of the present invention.

Then, a sealant containing a colored component which serves as the light absorption layer 40 is supplied into the flow channel (inner space S) through the inlet port 21 by using a syringe or the like. As shown in FIG. 13, the supplied sealant 40 flows in the flow channel and replaces the aqueous liquid 16 present outside the microwells 33 in the flow channel (inner space S). As a result, the light absorption layer 40 is formed as a sealant adjacent to the openings of the respective microwells 33 of the microwell array 30 disposed in the flow channel, and the aqueous liquid 16a is introduced into the respective microwells 33 of the microwell array 30. Thus, the aqueous liquid 16 can be easily sealed in the respective microwells 33 of the microwell array 30.

Then, electromagnetic waves (first electromagnetic waves) are irradiated onto the microwells 33, and the second electromagnetic waves (for example, fluorescence or phosphorescence) emitted from the components in the microwells 33 are detected. Among the microwells 33 that constitute the microwell array 30, the number of the microwells 33 that emit fluorescence or phosphorescence can be counted.

Since the light absorption layer 40 is located adjacent to the openings of the microwells 33 to seal the microwells 33, the light emitted from around the lid member 20 rather than the microwell array 30, is prevented from being observed.

In particular, as shown in FIG. 3, when the fluorescence reagent 16b is left in the flow channel at a position close to the lid member 20, the fluorescence emitted from the fluorescence reagent 16b left at a position close to the lid member 20 is also prevented from being incident on the microwells 33 so as not to disturb fluorescence emitted from the microwells 33, which is necessary for observation. Further, when the substrate 10 has autofluorescence, the autofluorescence of the substrate 10 is also prevented from being incident on the microwells 33. As a result, accurate observation can be performed by preventing a decrease in the S/N ratio of a fluorescence signal from the microwells 33.

The observation method of the present embodiment can be performed with use of a fluorescence microscope, for example. Further, irradiation of electromagnetic waves may be performed through the substrate of the microwell array, or through the wells, or from any direction. Further, detection of fluorescence or phosphorescence generated as a result of irradiation with the electromagnetic waves can be performed through the substrate of the microwell array, or through the wells (flow channel), or from any direction. For example, detection of fluorescence or phosphorescence with use of a fluorescence microscope can be conveniently performed through the substrate 10 of the microwell array 30 (the outer surface of the substrate 10, or the second surface of the substrate 10).

In the present embodiment, when a fluorescence microscope is used wherein the microscope is focused on the observation surface, which is the microwell array 30 corresponding to the microwells 33 in bright field, the microwells 33 can be observed with high precision and well-focused by virtue of the light absorption layer 40 which contains a colored component. Accordingly, detection in the fluorescence view can be performed with high precision.

According to the microfluidic device 1 of the present embodiment, the light absorption layer 40 contributes to improvement in precision of the fluorescence observation and reduction in operation time required for observation.

With reference to the drawings, a microfluidic device according to a second embodiment of the present invention will be described.

Figure 4:
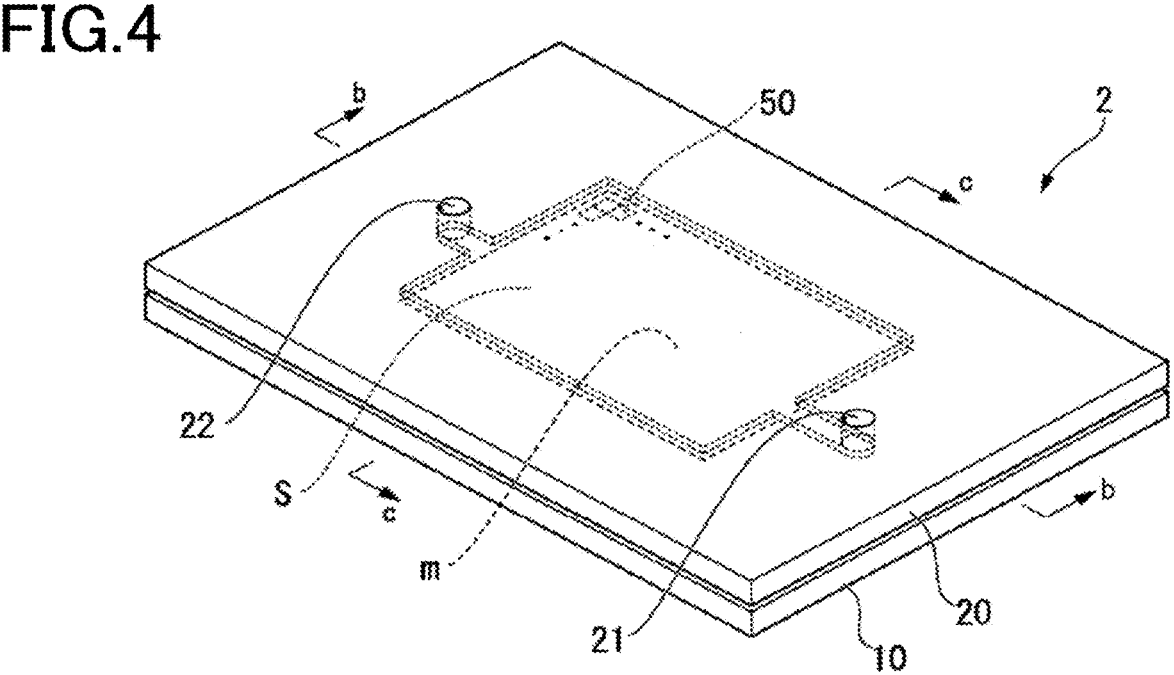
FIG. 4 is a perspective view of a microfluidic device according to a second embodiment of the present invention.

FIG. 4 is a perspective view of the microfluidic device of the present embodiment.

Figure 5:
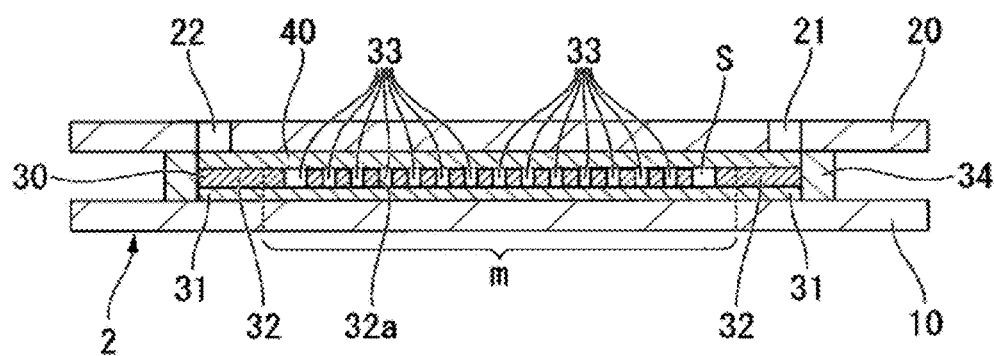
FIG. 5 is a cross-sectional view of the microfluidic device according to the second embodiment of the present invention.

FIG. 5 is a cross-sectional view (cross-sectional view taken along the arrow b-b of FIG. 4) of the microfluidic device according to the present embodiment.

The present embodiment differs from the above first embodiment in the microwell array area m. The components other than the microwell array area m are referred to by the same reference numerals, and the description thereof is omitted.

In the microfluidic device 2 according to the present embodiment, part of the flow channel is expanded compared to the flow channel of the microfluidic device 1 according to the above first embodiment in plan view (as viewed in the vertical direction to the microfluidic device 1). Further, the microwell array area m in the microfluidic device 2 has a larger area than the microwell array area m in the microfluidic device 1 in plan view (as viewed in the vertical direction). In the microwell array area m in the microfluidic device 2, the flow channel S is branched at the first hole 21, which is an inlet port, to communicate with a plurality of microwells 33, and the branches of the flow channel S are converged to the second hole 22, which is an outlet port. Accordingly, the microwell array area m may not necessarily be in a rectangular shape in plan view as shown in FIG. 4, and may be any shape such as a rhombus. Further, in the microfluidic device 2, operations such as measurement and observation can be performed without providing a flow channel.

Note that a plan view as described herein refers to a view of the microfluidic device or the microwell array as viewed in the direction perpendicular to the bottom member of the microfluidic device or the substrate of the microwell array.

In the present embodiment, the lid member 20 may be an autofluorescence layer. In this case as well, the light absorption layer 40 can prevent autofluorescence from the autofluorescence layer from disturbing the observation.

Moreover, in the present embodiment, the fluorescent beads 16*c* in the microwells 33 can be observed without observing fluorescence from the lid member 20, which is an autofluorescence layer. Although the light absorption layer 40 may be solid or liquid, liquid is selected if the light absorption layer 40 is provided by supplying into the flow channel S.

It is also possible that the target molecules are first captured by using the fluorescent beads 16*c* that specifically recognize the target molecules, and then the fluorescent beads 16*c* are accommodated in the microwells 33 and brought into contact with the fluorescent label that can specifically recognize the target molecules so that the target molecules can be labelled with fluorescence in the microwells 33.

In the present embodiment, the same effects as those of the above example can be achieved in the microwell array 30 that is expanded in plan view.

With reference to the drawings, a microfluidic device according to a third embodiment of the present invention will be further described.

The microfluidic device according to the third embodiment of the present invention differs from the microfluidic device according to the first embodiment of the present invention in that the wall layer 32 that constitutes the wall surface of the microwell array 30 in the microfluidic device 1 according to the first embodiment of the present invention shown in FIG. 2 is made of a material containing a colored component.

Accordingly, the present embodiment will be described with reference to FIG. 2, and the corresponding components are referred to by the same reference numerals and the description thereof is omitted except for the wall layer 32 that constitutes the wall surface of the microwell array 30 being made of a material containing a colored component.

In the present embodiment, since the wall layer 32 that constitutes the wall surface of the microwell array 30 in the microfluidic device 1 is made of a material containing a colored component, autofluorescence is reduced by the colored component even if the resin material of the wall layer 32 has autofluorescence to excitation light. As a result, autofluorescence around the microwells 33 is appropriately reduced, and disturbance in observation of the microwell 33 is appropriately prevented.

In the present embodiment, a member containing a colored component is used for the colored sealant (oil) and the wall layer 32.

Further, according to the microfluidic device of the present embodiment, since a particle diameter of the colored component contained in the wall layer 32 is in a predetermined range relative to a minimum dimension (minimum diameter) of the microwell 33, an effect of the fabrication precision of the microwells 33 can be prevented and an effect of autofluorescence in a sample analysis can be reduced.

Further, an inner wall surface of the microwells 33 are appropriately roughened by a particle of the colored component. As a result, a contact area between the sample and the microwells 33 increases, which improves sealing efficiency of the sample into the microwells 33.

Moreover, according to the microfluidic device of the present embodiment, even if a substance other than a resin (e.g., dust or the like) having autofluorescence is included in the material forming the wall layer 32, the excitation light is less likely to reach the substance since a colored component is present around the substance. Even if a small amount of excitation light reaches the substance, the generated autofluorescence is absorbed and eliminated by the colored component and is not likely to affect the sample analysis.

In addition, according to the microfluidic device of the present embodiment, since an interface between the substrate 10 and the wall layer 32 can be readily recognized, the microscope can be easily focused at around the bottom of the microwells 33 in sample observation. Accordingly, sample observation can be conveniently and suitably performed.

Further, since the wall layer 32 is colored, visual recognition of the wall layer 32 is improved. Accordingly, fabrication of the inner members such as the wall layer 32 of the microfluidic device can be favorably recognized. Accordingly, in fabrication of the microfluidic device 1, quality checks such as quality control and process control can be readily carried out.

Moreover, forgery prevention using color characteristics of the wall layer 32 is also possible. If the wall layer 32 is transparent, whether it is made of a predetermined resin or not cannot be determined from the outer appearance.

According to the present embodiment in which the wall layer 32 is made of a material containing a colored component such as ferrocyanide blue, a genuine product manufactured by the proper manufacturer can be readily distinguished from a fake product manufactured by a third party by means of an absorbed spectrum measured by a spectrophotometer even if the color is apparently the same.

The fluorescence wavelength used in the present embodiment may be any wavelength. For example, when detecting fluorescence having a peak in the wavelength range of 350 to 700 nm, which is a visible light range, colors such as blue, green, yellow, and red can be selected as colors of fluorescence to be generated so that different colors of fluorescence molecules are bound to different biomolecules to be detected. Accordingly, a plurality of biomolecules can be detected by one-time detection.

Here, use of black or blue as a colored component, which ensures absorption of electromagnetic waves in a wide wavelength range, is preferred due to high versatility.

Further, electromagnetic wave absorption properties of a colored component can be modified as appropriate depending on the fluorescence wavelength to be used, the wavelength of excitation light to be used, autofluorescence wavelength of dust which may be accumulated, or the like. Further, the wall layer may not necessarily completely absorb the electromagnetic waves of a predetermined wavelength as long as an effect of the above autofluorescence can be reduced to a degree that does not interfere with sample analysis. The term "a degree that does not interfere with sample analysis" means at least one-half or less, and more preferably one-fifth or less, of the fluorescence intensity of the detection target.

EXAMPLES

Examples of the present invention will be described below.

Example 1

Example 1 was conducted to confirm the effect of the microfluidic device as a biomolecule analysis kit with reduced fluorescence noise and the observation method according to the present invention.

In Example 1, an experiment was conducted to confirm that providing the light absorption layer that absorbs measurement wavelength or fluorescence wavelength can reduce fluorescence which causes the occurrence of noise.

<Fabrication of Array Device>

A 0.5 mm thick glass substrate was spin-coated with CYTOP (registered trademark) (manufactured by Asahi Glass Co., Ltd.), followed by baking at 180° C. for 1 hour. The formed CYTOP had a thickness of 3 μm. After spin-coated with CYTOP, the substrate was coated with a positive photoresist. Then, a pattern was formed by using a photomask. Subsequently, CYTOP was dry-etched by using $O_2$ plasma. The surface was washed and rinsed with acetone and ethanol to remove the photoresist left from the surface.

Each well (microchamber) formed by CYTOP had a diameter of 5 μm and a volume that ensured signal detection by an Invader reaction within a few minutes. In the microwell array area m, 100 blocks of the well arrays 50 were provided. Each block had 10,000 wells. Accordingly, a total of 1 million wells were formed on the substrate (laminate substrate). As shown in FIGS. 4 and 5, a glass plate having an introduction port (inlet port: not shown) and the substrate (laminate substrate, a base portion) were bonded to each other by using a 50 μm-thick double-sided adhesive tape.

<Supply of Mixed Solution of Sample and Detection Reaction Reagent>

An Invader reaction, which is a gene detecting technique, was used to confirm whether the occurrence of fluorescence noise can be reduced or not by providing a light absorption layer.

First, 22 μl of an invader reaction reagent (1 μm allele probe, 1 μm invader oligo, 1 μm FAM-labelled arm, 10 mM MOPS pH7.5, 6.25 mM MgCl2, 50 U/μL cleavase, Tween 20) and detection target DNA (detection reaction reagent) were supplied to an array device through an introduction port.

Subsequently, a solution in which black oil pastel was dissolved in squalene, which is a lipid that is not miscible with a detection reaction reagent was prepared as a solution for the light absorption layer. Then, 80 μl of the solution for the light absorption layer was supplied into the flow channel through the introduction port so that the reagent was delivered and sealed into the respective wells, and the light absorption layer was formed simultaneously. The solution in which black oil pastel was dissolved in squalene, which was a solution for the light absorption layer, was a solution obtained by dissolving 0.1 g of oil pastel in 1 mL=approx. 0.86 g of squalene (specific weight of squalene: 0.858). The solution was prepared to have a concentration of the oil pastel to the squalene in the solution for the light absorption layer of approximately 11 wt %.

Further, another sample was prepared as Comparative Example 1. In Comparative Example 1, a solution in which black pastel was not dissolved in squalene was supplied.

The sample of Example 1 and the sample of Comparative Example 1 were heated on a hot plate at 63° C. for 15 minutes to perform an Invader reaction.

Then, fluorescence in the respective wells was detected by using a fluorescence microscope (manufactured by Olympus Corporation) and NIBA fluorescence filter. The exposure time was 1000 msec.

Figure 7:
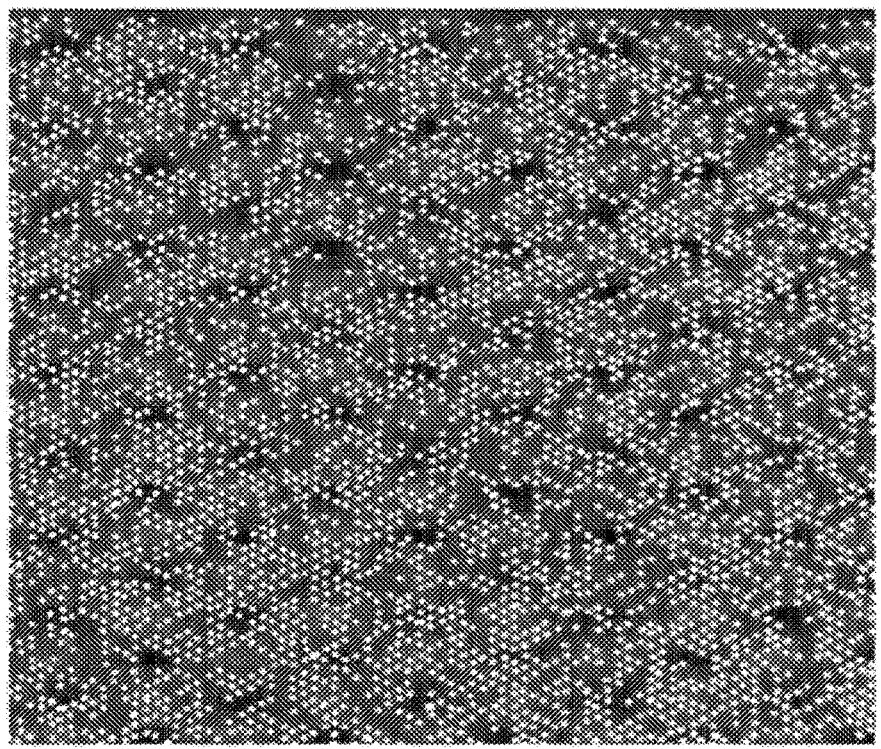
FIG. 7 is a fluorescence image according to a microfluidic device and an observation method in an example of the present invention in which a light absorption layer is provided.
Figure 8:
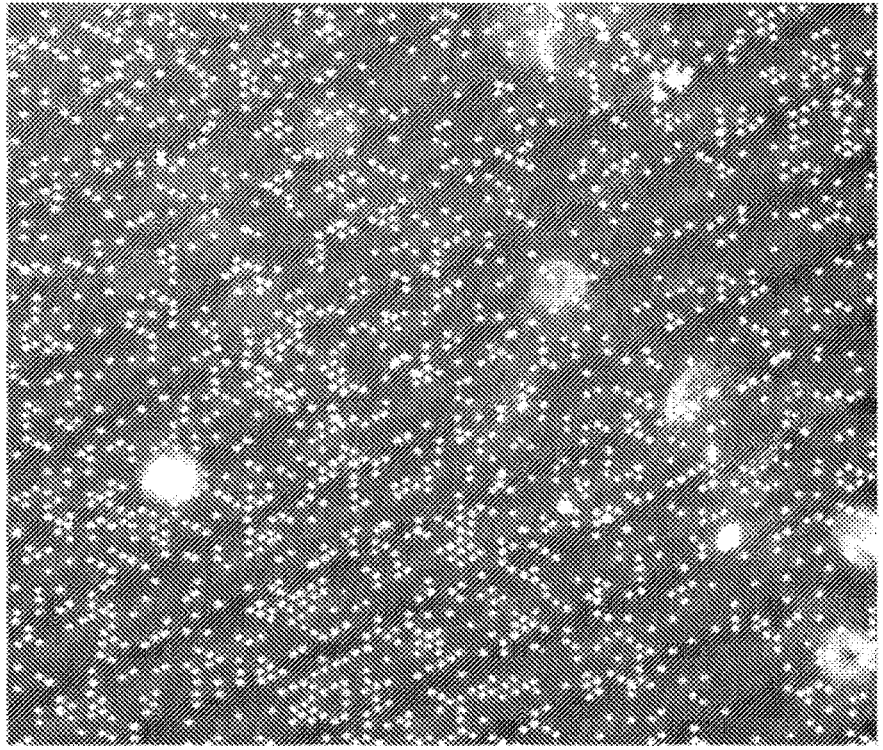
FIG. 8 is a fluorescence image according to a microfluidic device and an observation method in an example of the present invention in which a light absorption layer is not provided.

FIG. 7 is a fluorescence image according to Example 1 in which black pastel was dissolved in squalene and the light absorption layer was provided. Further, FIG. 8 is a fluorescence image according to Comparative Example 1 in which black pastel was not dissolved in squalene and the light absorption layer was not provided. Each magnification of the image is 10×.

Based on these results, in Example 1 in which the light absorption layer was provided, it was found that only the fluorescence from micro liquid droplets by the Invader reaction was clearly observed. On the other hand, in Comparative Example 1 in which the light absorption layer was not provided, it was found that a clear image was not obtained due to noise caused by fluorescence from the reactive liquid aggregation suspending in squalene (fluorescence reagent 16b in FIG. 3).

Example 2

The example was conducted to confirm the effect of the microfluidic device as a biomolecule analysis kit with reduced fluorescence noise and the fluorescence observation method according to the present invention.

Figure 6:
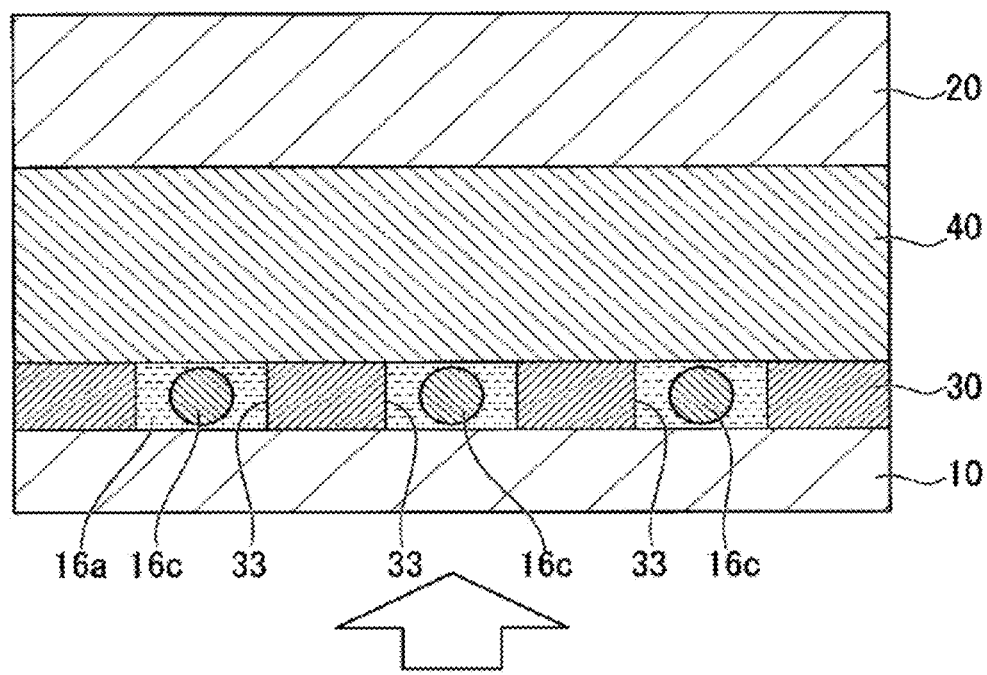
FIG. 6 is an enlarged cross-sectional view of the microfluidic device and an observation method according to the second embodiment of the present invention.

In this example, as viewed in the observation direction indicated by the arrow of FIG. 6 (as viewed from the lower surface of the microfluidic device, the outer surface of the substrate 10, or the second surface of the substrate 10 in FIG. 6), the lid member 20, which was a layer (autofluorescence layer) that emitted the same wavelength as the observation wavelength of the observation surface or a mirror layer (reflective layer) was located farther from the microwells 33 serving as the observation surface (constituting the observation surface). In this configuration, the fluorescent beads 16c were sealed in the microwells 33 to confirm whether occurrence of fluorescence noise can be reduced or not by providing the light absorption layer between the observation surface and the autofluorescence layer or between the observation surface and the reflective layer.

The array device in Example 2 was the same as the array device in Example 1. As the lid member 20, a plate of PET resin having autofluorescence was used instead of the glass plate. The fluorescent beads 16c of 3 μm were supplied into the array device through an introduction port.

Subsequently, a solution in which black pastel was dissolved in squalene, which is a lipid that is not miscible with a detection reaction reagent (the same oil pastel/squalene solution as that of Example 1) was prepared. Then, 80 μl of the solution was supplied into the flow channel through the introduction port so that the reagent was delivered and sealed into the respective wells, and the light absorption layer 40 was formed simultaneously.

Further, another sample was prepared as Comparative Example 2. In Comparative Example 2, a solution in which black pastel was not dissolved in squalene was supplied.

Then, fluorescence in the respective wells were detected by using a fluorescence microscope (manufactured by Olympus Corporation) and NIBA fluorescence filter. The exposure time was 50 msec.

Figure 9:
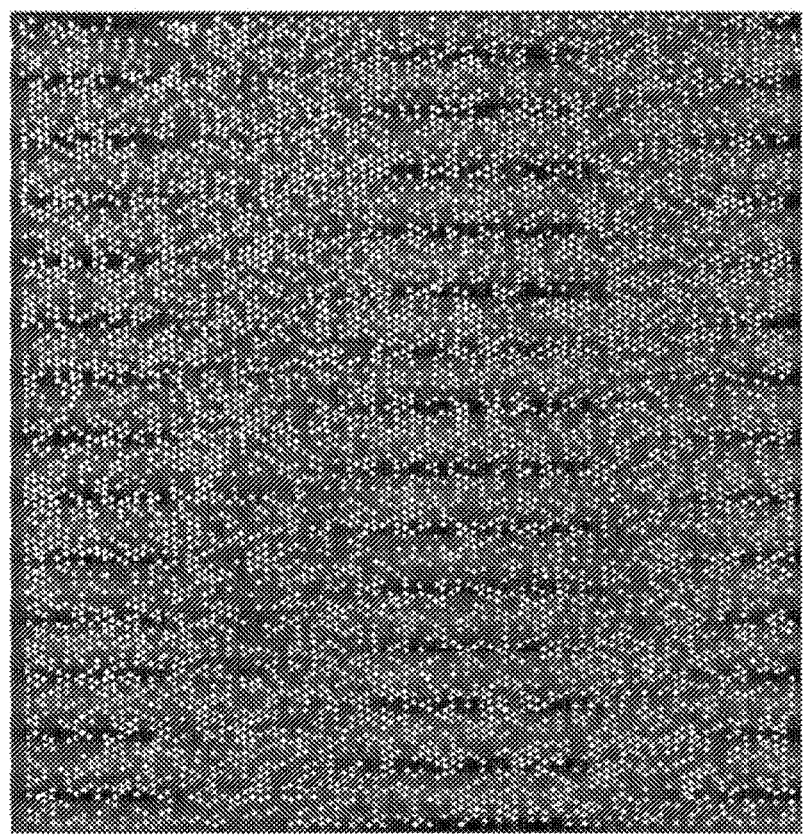
FIG. 9 is a fluorescence image according to a microfluidic device and an observation method in an example of the present invention in which a light absorption layer is provided.
Figure 10:
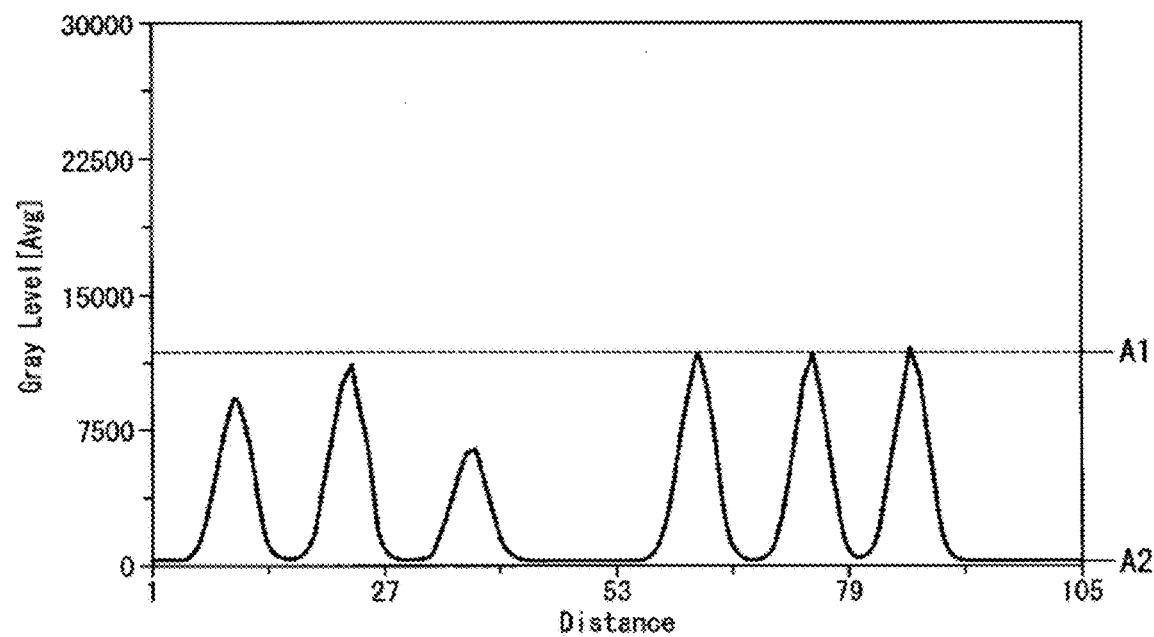
FIG. 10 is a diagram which shows the relationship between a distance and a fluorescence intensity based on line scan in FIG. 9.
Figure 11:
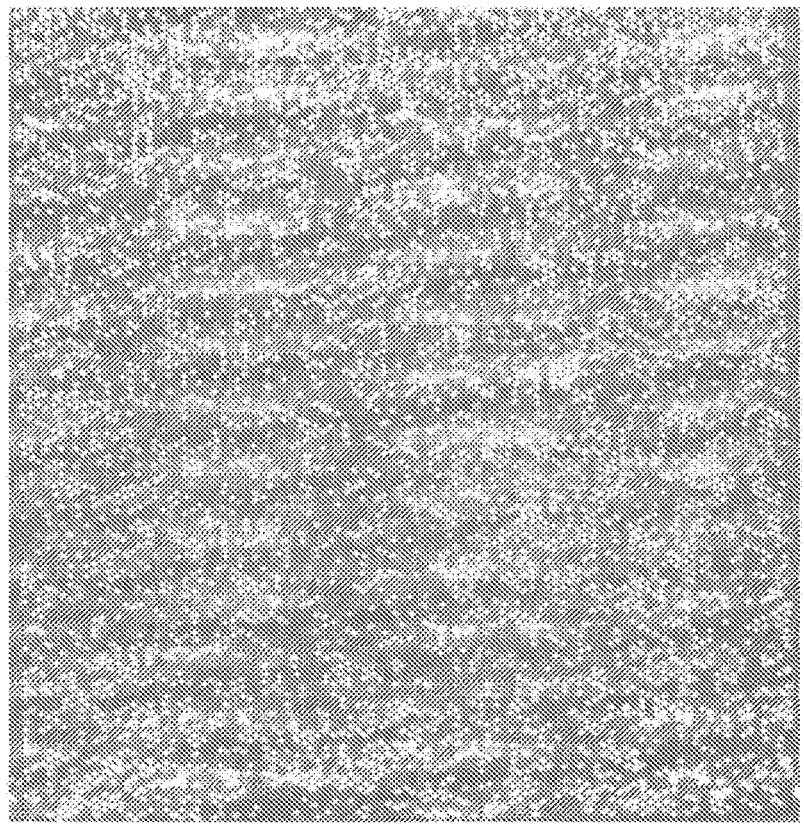
FIG. 11 is a fluorescence image according to a microfluidic device and an observation method in an example of the present invention in which a light absorption layer is not provided.
Figure 12:
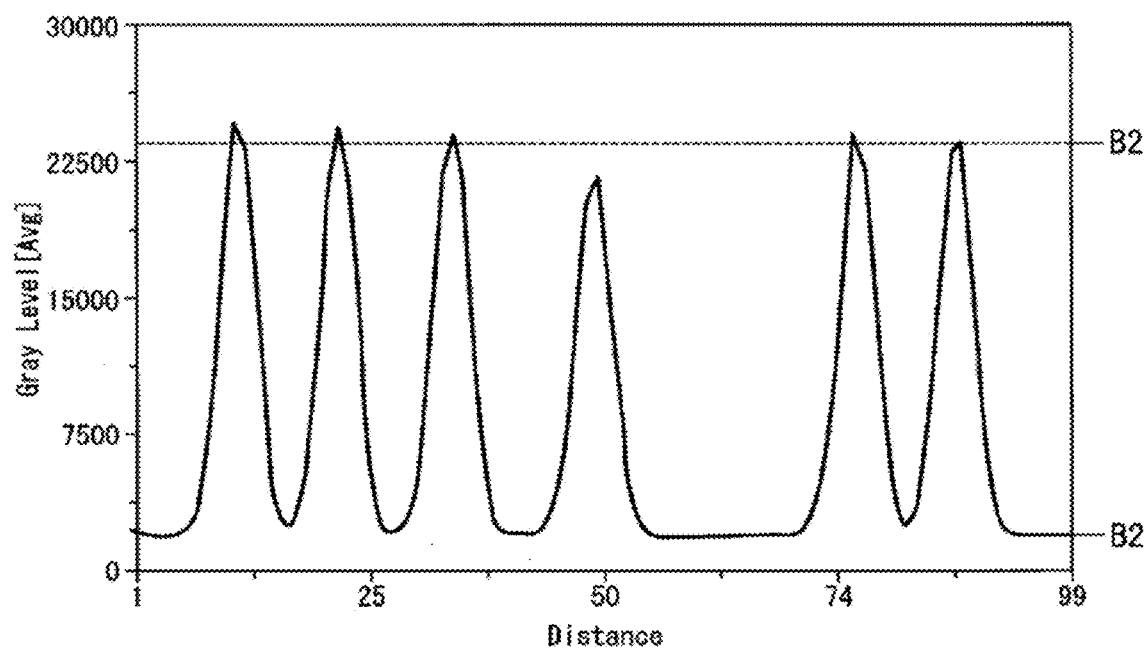
FIG. 12 is a diagram which shows the relationship between a distance and a fluorescence intensity based on line scan in FIG. 11.

FIG. 9 is a fluorescence image when black pastel was dissolved in squalene and the light absorption layer was provided. Further, FIG. 10 is a diagram obtained by line scan performed corresponding to FIG. 9, in which the horizontal axis represents a distance and the vertical axis represents a fluorescence intensity. Further, FIG. 11 is a fluorescence image when black pastel was not dissolved in squalene and the light absorption layer was not provided. Moreover, FIG. 12 is a diagram obtained by line scan performed corresponding to FIG. 11, in which the horizontal axis represents a distance and the vertical axis represents a fluorescence intensity. Each of the fluorescence intensities were compared to calculate the signal noise ratio (S/N ratio) as shown in Table 1. Each magnification of the image is 10×.

TABLE 1

|  | Signal (S) | Background (BG) | Sensor noise (SN) | S/N ratio (S-SN)/(BG-SN) |
|---|---|---|---|---|
| Light absorption layer is provided | 10000 | 180 | 100 | 124 |
| Light absorption layer is not provided | 23000 | 2000 | 100 | 12 |

The signal (S) refers to fluorescence emitted from an observation target (well area), and the noise (N) refers to fluorescence observed outside the observation target area. Further, since the noise inherent to the sensor occurs depending on the imaging conditions such as exposure time, a signal generated during imaging with the sample not being placed on the stage was subtracted from a fluorescence intensity of a signal generated during imaging of the sample (S and N). Further, the S/N ratio was calculated by averaging the fluorescence intensity values emitted from the well area, which were indicated as the wave lines in FIGS. 10 and 12.

The S/N ratio was 124 when the light absorption layer was provided, and was 12 when the light absorption layer was not provided. Based on these results, it was found that the occurrence of noise was obviously decreased when the light absorption layer was provided. In the present example, it was assumed that the occurrence of noise was attributed to autofluorescence emitted from the plate of PET resin. Accordingly, it was found that providing the light absorption layer can reduce a tendency of being affected by occurrence of fluorescence noise emitted from other than the observation surface so that a target sample can be observed. This effect is also effective to the case where a metal plate that reflects excitation light, as well as a plate having autofluorescence such as PET resin, is used as a cover, and the case where a liquid layer that generates fluorescence is provided.

Further, a microfluidic device and an observation method according to a third embodiment of the present invention will be described with reference to an example and a comparative example for confirming the effect.

Example 3

A 750 μm thick glass substrate was prepared as the substrate 10 having no autofluorescence.

As a material for the wall layer 32, a negative photoresist curable by exposure to light to which carbon black was added by 30 wt % was used. A material for the wall layer 32 was applied on the bottom layer 31 by spin coating at a thickness of 3 μm, pre-baked, and then exposed to light to thereby form the wall layer 32.

Conditions for pre-baking and exposure were determined as appropriate according to the photoresist used.

Thus, a laminate of Example 3 having a layer structure which corresponds to the microfluidic device of the third embodiment of the present invention was obtained.

Each well (microchamber) formed by a carbon black-containing wall layer had a diameter of 5 μm and a volume that ensures signal detection by an Invader reaction within a few minutes. In the microwell array area m, 100 blocks of the well arrays 50 were provided. Each block had 10,000 wells. Accordingly, a total of 1 million wells were formed on the laminate according to Example 3. As shown in FIGS. 4 and 5, a glass plate having an introduction port (inlet port:

not shown) and the laminate (a base portion) were bonded to each other by using a 50 μm-thick double-sided adhesive tape.

<Supply of Mixed Solution of Sample and Detection Reaction Reagent>

Whether fluorescence noise can be reduced or not by providing a light absorption wall layer and a light absorption layer was confirmed by using a fluorescence reagent solution containing fluorescein as a fluorophore.

First, 22 μl of a fluorescence reagent solution (1 μm fluorescein, 10 mM MOPS pH7.5, 6.25 mM MgCl2, 50 U/μL cleavase, Tween 20) was supplied to an array device via an introduction port.

For obtaining a background fluorescence intensity, fluorescence values of the wells which did not emit fluorescence were confirmed by using a reagent solution which did not contain fluorophore in the configuration where the light absorption wall layer and the light absorption layer were provided.

22 μl of a reagent solution (10 mM MOPS pH7.5, 6.25 mM MgCl2, 50 U/μL cleavase, Tween 20) was supplied to an array device via an introduction port.

Subsequently, a solution in which black oil pastel was dissolved in squalene, which is a lipid that is not miscible with a detection reaction reagent (the same oil pastel/squalene solution as that of Example 1) was prepared as a light absorption layer. Then, 80 μl of the light absorption layer was supplied through the introduction port so that the reagent was delivered and sealed into the respective wells, and the light absorption layer was formed simultaneously. Further, another sample was prepared as Comparative Example 3. In Comparative Example 3, a solution in which black pastel was not dissolved in squalene was supplied.

Then, fluorescence in the respective wells were detected by using a fluorescence microscope (manufactured by KEYENCE Corporation) and GFP fluorescence filter. The exposure time was 1.2 sec.

TABLE 2

|  | Signal (S) | Background (BG) | Sensor noise (SN) | S/N ratio (S-SN)/(BG-SN) |
|---|---|---|---|---|
| Light absorption layer is provided | 1800 | 1100 | 200 | 1.78 |
| Light absorption layer is not provided | 2600 | 2400 | 200 | 1.09 |

Table 2 shows a fluorescence intensity of a fluorescence solution (in Table 2, the value of the signal with the light absorption layer provided and with fluorescein contained), a fluorescence intensity of a solution containing no fluorescence (in Table 2, the value of the background with the light absorption layer provided and with fluorescein not contained) when black pastel was dissolved in squalene and the light absorption layer was provided, and a fluorescence intensity of a fluorescence solution (in Table 2, the value of the signal with the light absorption layer not provided and with fluorescein contained), and a fluorescence intensity of a solution containing no fluorescence (in Table 2, the value of the background with the light absorption layer not provided and the fluorescein not contained) when black pastel was not dissolved in squalene and the light absorption layer was not provided. Each of the fluorescence intensities were compared to calculate the signal noise ratio (S/N ratio). The signal (S) refers to fluorescence emitted from an observation target (well area), and the noise (N) refers to fluorescence observed outside the observation target area. The S/N ratio of the signal (S) and the noise (N) was calculated by averaging the fluorescence intensity values. The measurement methods of the fluorescence intensity and the S/N ratio were the same as those of Example 2.

The S/N ratio was 1.78 when the light absorption layer was provided, and was 1.09 when the light absorption layer was not provided. Based on these results, it was found that the occurrence of noise was obviously decreased when the light absorption wall layer and the light absorption layer were provided.

In the present example, it was assumed that the occurrence of noise was attributed to autofluorescence emitted from the plate of PET resin.

Accordingly, it was found that providing both the light absorption wall layer and the light absorption layer ensured observation with reduced occurrence of fluorescence noise emitted from other than the observation surface. This effect is also effective to the case where a metal plate that reflects excitation light, as well as a plate having autofluorescence such as PET resin, is used as a cover, and the case where a liquid layer that generates fluorescence is provided.

The present application addresses the following. When a fluorescence-emitting substance is present outside the wells serving as an observation area during observation of fluorescence of a sample by using a fluorescence microscope, it causes noise during observation. As a consequence, the target fluorescence cannot be clearly observed. In particular, the issue of noise generation is noticeable when fluorophores are left in oil that seals the wells or when a substrate located on the opposite side to the observation surface has autofluorescence.

Further, during observation of fluorescence of a sample by a fluorescence microscope, the fluorescence microscope should be focused on the well position, and such focusing is performed in bright field. However, there may be difficulty in focusing depending on the state of the well, leading to a decrease in observation precision.

The present invention has an aspect to provide a microfluidic device and an observation method as a biomolecule analysis kit with reduced fluorescence noise and a fluorescence observation method with high precision, respectively.

According to a first aspect of the present invention, a microfluidic device includes a substrate having electromagnetic wave transmission properties, a lid member disposed opposite to the substrate in a state of being separated from the substrate, a flow channel, which has a light absorption layer that absorbs electromagnetic waves of a predetermined wavelength, disposed between the substrate and the lid member, and a microwell array formed on the substrate and having a plurality of microwells that are open to the flow channel and allow an analysis target to be introduced into the microwells.

The light absorption layer may include a light absorption material that absorbs light of wavelength corresponding to the analysis target.

The light absorption layer may be liquid.

The liquid provided as the light absorption layer may be liquid that is not readily miscible with aqueous liquid introduced into the microwells.

The light absorption layer may include a colored component.

According to a second aspect of the present invention, a fluorescence observation kit includes the microfluidic device according to the above aspect.

According to a third aspect of the present invention, an observation method includes preparing the microfluidic device according to the above aspect, supplying aqueous liquid including the analysis target into the flow channel to introduce the aqueous liquid into the microwells, supplying the light absorption layer as a sealant into the flow channel to form the light absorption layer as a sealing layer on the aqueous liquid introduced into the microwells to thereby seal the aqueous liquid in the microwells, irradiating first electromagnetic waves onto the microwells, and detecting second electromagnetic waves emitted from the microwells.

The microwells may be observed through an outer surface of the substrate after the electromagnetic wave is irradiated onto the microwells.

An observation surface located inside the microwells may be in contact with the light absorption layer, and the analysis target may be detected on the observation surface.

The light absorption layer may be located farther from the observation surface located inside the microwells in an observation direction, and the analysis target may be detected on the observation surface.

A substance including the analysis target introduced inside the microwells may include any of DNAs, RNAs, miRNAs, mRNAs, proteins, and cells, and the analysis target may be any of DNAs, RNAs, miRNAs, mRNAs, and proteins.

A signal from an enzymatic reaction may be detected when the enzymatic reaction is performed in the aqueous liquid disposed on the observation surface located inside the microwells.

The analysis target may be nucleic acid, and the enzymatic reaction may be Invader reaction.

According to a fourth aspect of the present invention, a light absorbing agent for a light absorption layer is provided, wherein the light absorbing agent includes a material that absorbs electromagnetic waves of a predetermined wavelength, and the material is used for a microfluidic device including a substrate having electromagnetic wave transmission properties, a lid member disposed opposite to the substrate in a state of being separated from the substrate, a flow channel disposed between the substrate and the lid member and adapted so that the material is disposed in the flow channel, and a microwell array formed on the substrate and having a plurality of microwells that are open to the flow channel and allow an aqueous liquid including an analysis target to be introduced into the microwells, disposed on the aqueous liquid, and configured to absorb the electromagnetic waves.

According to a fifth aspect of the present invention, a method for reducing noise is provided, wherein the light absorbing agent according to the above aspect is used to reduce the occurrence of noise in measurement target electromagnetic waves emitted from the microfluidic device.

According to a sixth aspect of the present invention, a method for reducing noise is provided, wherein a wall of the microwells is colored, in addition to the light absorbing agent according to the above aspect, to thereby reduce the occurrence of noise in measurement target electromagnetic waves emitted from the microfluidic device.

The microfluidic device according to the above aspect of the present invention includes a substrate having electromagnetic wave transmission properties, a lid member disposed opposite to the substrate in a state of being separated from the substrate, a flow channel, which has a light absorption layer that absorbs electromagnetic waves of a predetermined wavelength, disposed between the substrate and the lid member, and a microwell array formed on the substrate and having a plurality of microwells that are open to the flow channel and allow an analysis target to be introduced into the microwells.

Accordingly, the light absorption layer is disposed in the flow channel, which is located farther from the observation surface inside the microwells in the observation direction as viewed through the outer surface of the substrate (viewed from the substrate).

Accordingly, fluorescence generated outside the well which is the observation area can be shielded by the light absorption layer to reduce fluorescence which may cause the occurrence of noise during observation, even if fluorophores are left in the flow channel or if the lid member has autofluorescence. As a result, the S/N ratio can be improved, which enables clear observation of target fluorescence. According to the microfluidic device of the above aspect, colored sealant can be applied as a light absorption layer. This can reduce fluorescence emitted onto the microwells from a fluorescence-emitting substance present in a non-observation area so that the occurrence of noise during measurement can be reduced and measurement with high precision can be achieved. Accordingly, a microfluidic device with improved observation precision can be provided.

According to the microfluidic device of the above aspect of the present invention, the light absorption layer includes the light absorption material that absorbs light of wavelength corresponding to the analysis target (observation light). Accordingly, fluorescence generated outside the well which is the observation area (fluorescence generated outside the observation area) can be absorbed by the light absorption layer to reduce fluorescence which may cause the occurrence of noise during observation, even if fluorophores are left in the flow channel or if the lid member has autofluorescence.

The observation light may have a wavelength of a fluorescence wavelength or an excitation wavelength, or alternatively, both a fluorescence wavelength and an excitation wavelength. That is, the light absorption layer can include a substance that absorbs observation light which is light having fluorescence wavelength or light having excitation wavelength, or alternatively, both light having a fluorescence wavelength and light having an excitation wavelength.

According to the microfluidic device of the above aspect of the present invention, the light absorption layer, which is liquid, provides the light absorption layer as a sealing layer on the upper side of the aqueous liquid including an analysis target substance (analysis target) introduced into the microwells. Accordingly, fluorescence generated outside the well which is the observation area can be absorbed by the light absorption layer to reduce fluorescence which would cause noise during observation, even if fluorophores are left in the sealing layer or if the lid member has autofluorescence. Moreover, since the light absorption layer can be formed only by filling the flow channel with liquid as a sealing layer, there is no need to increase the number of operation processes and the number of components in order to improve the S/N ratio by reducing the occurrence of noise and to improve observation precision.

According to the microfluidic device of the present invention, since the liquid serving as the light absorption layer is liquid that is not readily miscible with aqueous liquid introduced into the microwells, the liquid serving as the light absorption layer located adjacent to the openings of the microwells remains not readily miscible with aqueous liquid introduced into the microwells. Accordingly, the liquid serving as the light absorption layer seals liquid in the microwells. Further, fluorescence generated outside the well which is the observation area (fluorescence generated outside the observation area) can be absorbed by the light absorption layer to reduce fluorescence which may cause noise during observation.

The liquid constituting the light absorption layer may be liquid that is not readily miscible with water, which is lipophilic liquid, for example.

According to the microfluidic device of the above aspect of the present invention, the light absorption layer includes a colored component. Accordingly, fluorescence generated outside the well which is the observation area (fluorescence generated outside the observation area) can be absorbed by the light absorption layer to reduce fluorescence which may cause the occurrence of noise during observation. Furthermore, liquid other than the colored component in the light absorption layer can effectively seal liquid in the microwells.

The fluorescence observation kit according to the above aspect of the present invention includes the microfluidic device according to the above aspect. Accordingly, it is possible to provide a fluorescence observation kit which improves the S/N ratio by reducing the occurrence of noise and improves observation precision without increasing the manufacturing cost due to an increase in operation processes and the number of components.

The observation method according to the above aspect of the present invention includes preparing the microfluidic device according to the above aspect, supplying aqueous liquid including the analysis target into the flow channel to introduce the aqueous liquid into the microwells, supplying the light absorption layer as a sealing liquid into the flow channel to form the light absorption layer as a sealing layer on the aqueous liquid introduced into the microwells to thereby seal the aqueous liquid in the microwells, irradiating first electromagnetic waves onto the microwells, and detecting second electromagnetic waves (for example, fluorescence or phosphorescence) emitted from the microwells.

According to the observation method of the above aspect, the light absorption layer is disposed in the flow channel, which is located farther from the observation surface inside the microwells in the observation direction as viewed through the outer surface of the substrate (viewed from the substrate) so that the light absorption layer as a sealing layer is formed on the aqueous liquid including an analysis target substance (analysis target) introduced into the microwells. Further, fluorescence generated outside the well which is the observation area (fluorescence generated outside the observation area) can be shielded or absorbed by the light absorption layer even if fluorophores are left in the sealing layer or if the lid member has autofluorescence. Moreover, since the light absorption layer can be formed only by filling the flow channel with liquid as a sealing layer, there is no need to increase the number of operation processes and the number of components in order to improve the S/N ratio by reducing the occurrence of noise and to improve observation precision.

According to the observation method of the above aspect of the present invention, the microwells are observed through the outer surface of the substrate (from the substrate) after the electromagnetic waves are irradiated onto the microwells. Accordingly, fluorescence which may cause noise during observation can be reduced.

According to the observation method of the present invention, the observation surface located inside the microwells is in contact with the light absorption layer and the analysis target is observed on the observation surface, or alternatively, the light absorption layer is located farther from the observation surface in the observation direction and the analysis target is detected on the observation surface. Accordingly, the occurrence of noise during observation of the microwells in the fluorescence view can be reduced. Further, accurate observation and reduction in operation time can be achieved by performing accurate and prompt focusing when focusing is performed in bright field to be focused at the observation surface located inside the microwells. In addition, a clear fluorescence observation can also be performed.

According to the observation method according to the above aspect of the present invention, a substance including the analysis target introduced inside the microwells may include any of DNAs, RNAs, miRNAs, mRNAs, proteins, and cells, and the analysis target may be any of DNAs, RNAs, miRNAs, mRNAs, and proteins.

According to the observation method according to the above aspect of the present invention, a signal from an enzymatic reaction can be detected when the enzymatic reaction is performed in the aqueous liquid (micro liquid droplets) disposed on the observation surface located inside the microwells.

According to the observation method according to the above aspect of the present invention, the analysis target may be nucleic acid, and the enzymatic reaction may be an Invader reaction.

The light absorbing agent for a light absorption layer according to the above aspect of the present invention includes a material that absorbs electromagnetic waves of a predetermined wavelength, and the material is used for a microfluidic device including a substrate having electromagnetic wave transmission properties, a lid member disposed opposite to the substrate in a state of being separated from the substrate, the flow channel disposed between the substrate and the lid member and adapted so that the material is disposed in the flow channel, and a microwell array formed on the substrate and having a plurality of microwells that are open to the flow channel and allow an aqueous liquid including an analysis target to be introduced into the microwells, disposed on the aqueous liquid, and configured to absorb the electromagnetic waves.

According to the method for reducing noise according to the above aspect of the present invention, the light absorbing agent according to the above aspect is used to reduce the occurrence of noise in measurement target electromagnetic waves emitted from the microfluidic device.

According to the method for reducing noise according to the above aspect of the present invention, a wall of the microwells is colored, in addition to the light absorbing agent according to the above aspect, to thereby reduce the occurrence of noise in measurement target electromagnetic waves emitted from the microfluidic device.

The above aspects can solve the following problem: when an enzymatic reaction is performed in microchambers (microwells) having a volume of 1 nanoliter (nl) or less to observe fluorescence by using a fluorescence microscope, a fluorescence-emitting substance, if present outside the observation area (in the non-observation area), causes the occurrence of noise during observation, which leads to a failure in clear observation of a target fluorescence. Further, according to the above aspects, an effect can be obtained that a microfluidic device and an observation method which reduce fluorescence noise from the non-observation target to ensure clear fluorescence observation can be provided.

INDUSTRIAL APPLICABILITY

As an exemplary application, the present invention is applicable to a vessel for light measurement via a substrate as described in the present application, or an application of blocking a noise component during light measurement.

REFERENCE SIGNS LIST 1, 2 . . . Microfluidic device
10 . . . Substrate
20 . . . Lid member (cover)
30 . . . Microwell array (micropore array layer)
33 . . . Microwell (micropore)
40 . . . Light absorption layer
50 . . . Well array
16 . . . Liquid, aqueous solution, aqueous liquid
16a . . . Detection reaction reagent (liquid, aqueous solution, aqueous liquid in well)
16b . . . Detection reaction reagent (outside the well, aqueous liquid outside the well)
16c . . . Fluorescent beads
A1 . . . Fluorescence intensity (signal)
A2 . . . Fluorescence intensity (background)
B1 . . . Fluorescence intensity (signal)
B2 . . . Fluorescence intensity (background)
S . . . Flow channel (inner space)
m . . . Microwell array area Obviously, numerous modifications and variations of the present invention are possible in light of the above teachings. It is therefore to be understood that within the scope of the appended claims, the invention may be practiced otherwise than as specifically described herein.

What is claimed is:

1. A microfluidic device, comprising:
a substrate having an electromagnetic wave transmission property;
a micropore array layer formed on the substrate and having a plurality of microwells such that the plurality of microwells is formed in a microarray area of the micropore array layer and has a plurality of openings, respectively;
a lid member facing the substrate and separated from the substrate such that the lid member covers the micropore array layer on the substrate and forms a flow channel extending between the lid member and the microarray area of the micropore array layer and directly over the plurality of openings of the plurality of microwells and that the flow channel is directly communicated to the plurality of microwells through the plurality of openings and supplies an aqueous liquid comprising a target of analysis to the plurality of microwells between the substrate and the lid member; and
a light absorption layer comprising liquid and filling the flow channel between the micropore array layer and the lid member such that the light absorption layer is configured to absorb an electromagnetic wave corresponding to an observation light of the target of analysis and shields the plurality of microwells in the micropore array layer from the electromagnetic wave from the lid member and that the liquid of the light absorption layer is not readily miscible with the aqueous liquid and covers the aqueous liquid in the plurality of microwells.

2. The microfluidic device of claim 1, wherein the light absorption layer includes a light absorption material that absorbs light of a wavelength in accordance with the target of analysis.

3. The microfluidic device of claim 1, wherein the micropore array layer comprises a bottom layer positioned on the substrate and a wall layer formed on the bottom layer such that the wall layer has the plurality of microwells formed in a microwell array area of the wall layer and having the plurality of openings at the flow channel, respectively.

4. The microfluidic device of claim 1, wherein the lid member has an inlet port at one end of the flow channel and an outlet port at an opposite end of the flow channel such that the plurality of microwells is formed in the microwell array area between the inlet port and the outlet port.

5. The microfluidic device of claim 3, wherein the liquid of the light absorption layer is an oil-based sealant.

6. The microfluidic device of claim 4, wherein the liquid of the light absorption layer is an oil-based sealant.

7. The microfluidic device of claim 1, wherein the light absorption layer includes a colored component dispersed in the liquid.

8. A fluorescence observation kit, comprising:
the microfluidic device of claim 1.

9. A method of detecting a target of analysis, comprising:
supplying the aqueous liquid including the target of analysis into the flow channel such that the aqueous liquid is introduced into the microwells in the microfluidic device of claim 1 prior to forming the light absorption layer in the microfluidic device;
forming the light absorption layer of the microfluidic device on the aqueous liquid introduced into the microwells such that the aqueous liquid is sealed in the microwells by the light absorption layer;
irradiating a first electromagnetic wave onto the microwells; and
detecting a second electromagnetic wave of the observation light emitted from the microwells.

10. The method of claim 9, wherein the detecting is conducted through an outer surface of the substrate after the irradiating of the first electromagnetic wave.

11. The method of claim 10, wherein the detecting is conducted on an observation surface located inside the microwells, which is in contact with the light absorption layer.

12. The method of claim 10, wherein the detecting is conducted on an observation surface located inside the microwells, and the light absorption layer is located farther from the observation surface.

13. The method of claim 11, wherein the target of analysis is one of DNA, RNA, miRNA, mRNA, and protein.

14. The method of claim 12, wherein the target of analysis is one of DNA, RNA, miRNA, mRNA, and protein.

15. The method of claim 11, wherein the detecting comprises detecting a signal from an enzymatic reaction when the enzymatic reaction occurs in the aqueous liquid applied on the observation surface.

16. The method of claim 12, wherein the detecting comprises detecting a signal from an enzymatic reaction when the enzymatic reaction occurs in the aqueous liquid applied on the observation surface.

17. The method of claim 15, wherein the target of analysis is nucleic acid, and the enzymatic reaction is an Invader reaction.

18. The microfluidic device of claim 1, wherein the liquid of the light absorption layer comprises a sealant and a light absorbent substance soluble in the sealant.

19. The microfluidic device of claim 1, wherein the micropore array layer is integrally molded with the substrate.

20. The method of claim 9, wherein the micropore array layer is integrally molded with the substrate.

\* \* \* \* \*